April 17, 1962 G. MERRILL Plant Pat. 2,138

NECTARINE TREE

Filed April 10, 1961

WITNESS

Addison E. Avery

INVENTOR

GRANT MERRILL

HUEBNER & WORREL

ATTORNEYS

BY Richard M. Worrel

United States Patent Office

Plant Pat. 2,138
Patented Apr. 17, 1962

2,138
NECTARINE TREE
Grant Merrill, Red Bluff, Calif.
Filed Apr. 10, 1961, Ser. No. 102,078
1 Claim. (Cl. 47—62)

The present invention relates to a nectarine tree and more particularly to a new and distinct variety thereof, broadly characterized by being a strong vigorous tree which bears very early, red mottled, firm clingstone to slightly freestone, fruit.

The fruit of the subject variety most nearly resembles that of the Merrill Sunrise nectarine (Plant Patent No. 1,256) but is an improvement thereon in its ripening from three to ten days, average one week, earlier, with a brighter yellow under color and a brighter, more contrasting red over color and with fewer speckles.

Because of the rich soil and favorable climatic environment prevailing in most of the commercial nectarine farming areas of California, the nectarine trees tend to produce rank growth and dense shade resulting in serious impairment of the coloring of the fruit. Inasmuch as most fruits rely on eye appeal for their sales, color impairment is highly undesirable. A primary object to the plant breeding procedures which have resulted in the development of this new nectarine variety has been to achieve a highly colored red nectarine which maintains its color even under conditions of rank growth and dense shade.

Another object was to provide a nectarine tree characterized by the production of brightly colored fruit which has good shipping and storage qualities.

Another object was to provide a nectarine tree of the general type shown and described in Plant Patent No. 1,256 but which produces fruit which ripens earlier.

A further object has been to produce a new nectarine variety characterized by moderate but consistent fruit set minimizing pruning and thinning requirements without being subject to irregular production.

Further objects and advantages will become more fully apparent in the subsequent description in the specification.

Figure 1:
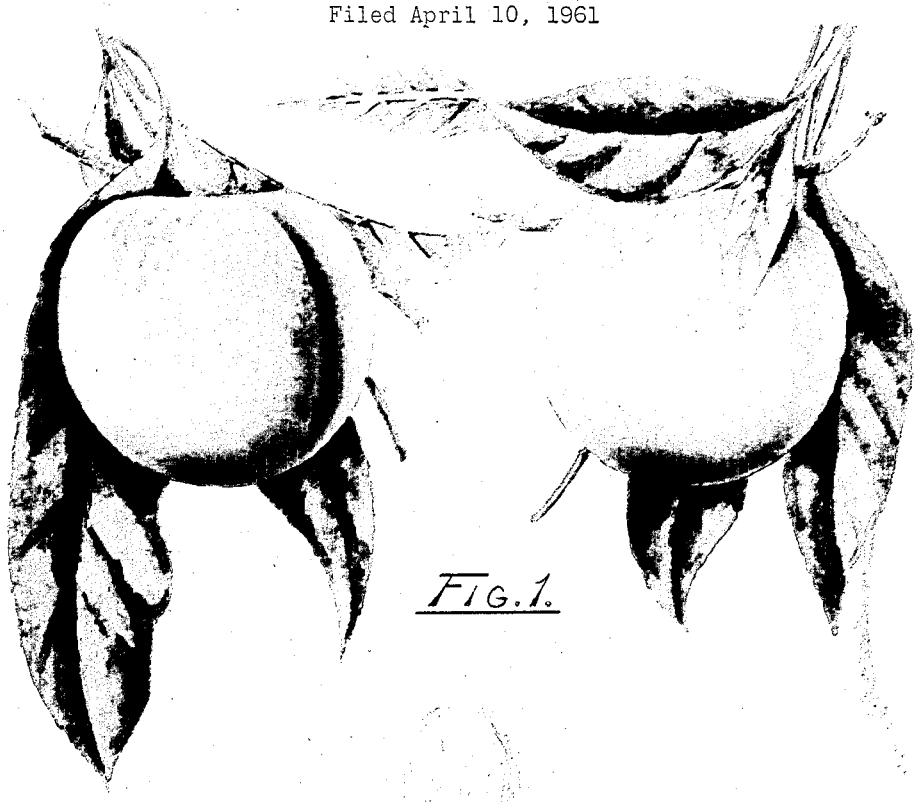
FIG. 1 is a water color painting of a pair of fruit bearing twigs having leaves and mature fruit thereon characteristic of the instant variety. The fruit on the left was grown in virtually full sun and the one on the right was grown where heavily shaded by leaves and thus shows yellow under color.
Figure 2:
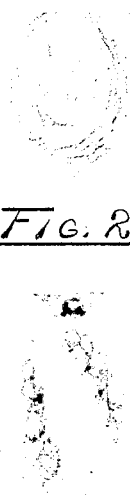
FIG. 2 is a water color painting of a pit of the variety when dried.
Figure 3:
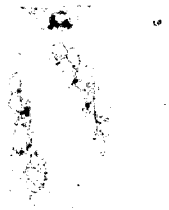
FIG. 3 is likewise a water color painting and shows a fruit sectioned on its suture plane to show certain cling characteristics but with evident partial freeing of the removed stone.

The most distinctive characteristics in the instant variety of nectarine tree are its very early ripening of its fruit, its brilliant skin coloring and the strong vigorous growing habits of the tree.

This new variety of nectarine was produced by me on my farm near Red Bluff, Tehama County, California, as an open pollinated embryo cultured seedling of Merrill Sunrise (Plant Patent No. 1,256). The present variety was asexually propagated by budding onto a seedling tree in my virus isolation plot at Corning, Tehama County, California, in 1958. When this bud came into bearing in 1960, fruit and other characteristics of this nectarine proved to be identical to the original nectarine tree resulting from the cultured seedling.

Referring more specifically to the pomological characteristics of this new and distinct variety of nectarine tree, the following have been observed under the ecological conditions prevailing at my farm near Red Bluff, Tehama County, California and is an outline description thereof. All major color plate identifications are by reference to Maerz and Paul Dictionary of Color.

*Tree*

Shape: Medium size, vigorous, medium upright, medium dense, vase shaped by usual pruning practices. Productive and a regular bearer.

Trunk: Medium size, medium shaggy, dull grey.

Branches: Medium shaggy, dull grey on older branches, grey brown on younger branches. Lenticels—numerous, medium size.

Leaves (selected from midportion of vigorous unbranched terminal shoots 12" to 18" long):

*Length.*—5" to 7", average 6".

*Width.*—1" to 1½", average 1¼".

*Form.*—Lanceolate, tip acuminate, medium thick.

*Color.*—Upper surface medium light green (22–L–7). Underside of leaf light green (21–K–6). Heavy under midrib greenish yellow (18–K–2).

*Class* (Meader and Blake: Proceedings Am. Soc. Hor. Sc., vol. 37, page 206).—Class 2. Width.—length ratio, .20 to .30, average .254. Apex angle (1" from tip)—32° to 50°, average 40°. Base angle (½" from petiole)—40° to 60°, average 55°.

*Margin.*—Crenate.

*Petiole.*—Medium length, medium slender.

*Stipules.*—At base of leaf, falling off early.

*Glands.*—None to 4, average 2, mostly alternate, small, reniform. Color—mostly green. Position—on petiole and at base of leaf.

Flower buds: Medium size, plump, free, pubescent.

Flowers: Midseason to late bloom, about in season with Merrill Sunrise (Plant Patent No. 1,256). Large, showy, pink color.

*Anthers.*—Yellow with some orange.

*Pollen.*—Abundant.

*Fruit*

Maturity when described—firm ripe. Approximately June 10 to June 17.

Size: Uniform, medium size.

*Axial diameter.*—2⅛" to 2½", average 2 5/16".

*Transverse in suture plane.*—2¼" to 2½", average 2⅜".

*At right angles to suture plane (cheek to cheek).*—2⅛" to 2⅜", average 2¼".

Form: Generally globose, compressed slightly axially.

*Suture.*—Distinct, shallow, deeper at the base. Extends from base to apex. Has slight depression beyond pistil point.

*Ventral surface.*—Slightly lipped toward base, lips equal and unequal.

*Cavity.*—Flaring, rounded, elongated in suture plane with suture showing on both sides. Depth—⅛" to ¼"; breadth—½" to ¾". Markings—green to red depending on how much cavity is shaded.

*Base.*—Truncate.

*Apex.*—Rounded, pistil point apical, small, sometimes non-existant.

*Stem.*—Length, about ⅛" to 3/16"; diameter, about ⅛". Usually free from stone but adheres occasionally.

*Skin.*—Medium thick, medium tender, tenacious to flesh. Tendency to crack—none. Color—under color where shaded—bright orange yellow (10–L–6) and where exposed to sun, orange yellow (10–J–7) to dark orange (3–D–12); over color— medium orange red (4–L–10) to darker red (7–L–8). Some darker red mottles or stripes occur (5–L–11).

Flesh:

*Color.*—From golden yellow near the stem end (9–L–3) to deep chrome yellow (9–L–7) at the apical end.

*Amygdalin.*—Moderate.

*Juice.*—Moderate.

*Texture.*—Firm, meaty, melting.

*Fibers.*—Few, fine.

*Ripens.*—Evenly to slightly earlier at the apex.

*Flavor.*—Milk, subacid, delicate.

*Aroma.*—Distinct.

*Eating quality.*—Good.

Stone: Cling to slightly free when ripened off the tree.

*Fibers.*—Short.

*Size.*—Length, 1⅛" to 1⅜", average 1 3/16"; breadth ⅞" to 1 1/16", average 1".

*Form.*—Elliptical to ovoid, tendency to cuneate toward base.

*Base.*—Straight to slightly oblique.

*Hilum.*—Oval.

*Apex.*—Acuminate.

*Sides.*—Unequal, flattened on either side.

*Surface.*—Unequally furrowed throughout. Ridged throughout. Pitted from base to above center. Ridges jagged. Pits elongated.

*Ventral edge.*—Thick, without wing.

*Dorsal edge.*—Full shallow groove toward base, ridges continuous.

*Color.*—In flesh, orange tan (5–A–11); when dry, light tan (11–D–4) to medium tan (11–J–7).

Use: Market, local, dessert, long distance shipping.

Shipping quality: Good.

It is to be understood that normal variations in the described characteristics of the new variety nectarine tree result from environmental changes, such as in climate and soil conditions, and from changes in cultural practices, such as in pruning, thinning, fertilizing, spraying, irrigating and the like. The description is that of the variety produced under the conditions prevailing at my farm near Red Bluff, Tehama County, California and the characteristics are found to hold true in asexual reproduction of the variety.

Having thus described and illustrated by new variety nectarine tree, what I claim as new and desire to secure by Letter Patent is:

A new and distinct variety of nectarine tree substantially as illustrated and described, characterized by its very early ripening fruit with brilliant red mottled skin coloring, its freeing from the stone when ripened off of the tree, and its strong vigorous trees, and as compared with Merrill Sunrise nectarine (Plant Patent No. 1,256), being an improvement thereon by its fruit ripening about a week earlier and having a brighter skin color with fewer speckles.

No references cited.